United States Patent [19]
Mayer et al.

[11] 3,970,674
[45] July 20, 1976

[54] CERTAIN HEXAHYDRO-2-LOWERALKOXY-5-OXYCYCLOPENTA [b] FURANS CONTAINING AN OLEFINIC SUBSTITUENT IN THE 4-POSITION

[75] Inventors: Hans Johann Mayer, Fullinsdorf; Albert Eduard Fischli, Basel, both of Switzerland; Michael Josef Klaus, Weil am Rhein, Germany; Alexander Eduard Wick, Riehen, Switzerland

[73] Assignee: Hoffmann-La Roche Inc., Nutley, N.J.

[22] Filed: Sept. 10, 1975

[21] Appl. No.: 612,068

Related U.S. Application Data

[62] Division of Ser. No. 374,850, June 9, 1973, abandoned.

[30] Foreign Application Priority Data
July 6, 1972    Switzerland....................... 10120/72

[52] U.S. Cl................ 260/346.2 R; 260/240 A; 260/240 D; 260/240 R; 260/514 D; 260/343.3 R; 260/345.9; 260/345.8
[51] Int. Cl.$^2$........................................ C07D 307/93
[58] Field of Search................. 260/346.2 R, 345.9, 260/345.8, 240 R, 240 A, 240 D

[56] References Cited
OTHER PUBLICATIONS
Corey et al., Tetrahedron Letters 4, p. 311–313, (1970).

*Primary Examiner*—Natalie Trousof
*Assistant Examiner*—Bermard Dentz
*Attorney, Agent, or Firm*—Samuel L. Welt; Bernard S. Leon; Richard A. Gaither

[57] ABSTRACT

Process for synthesizing a prostaglandin from a hexahydro-4-(lower alkoxy)-2H-oxireno[3,4]cyclopenta[1,2-b]furan, utilizing as an intermediate in the process a hexahydro-5-hydroxy-2-lower alkoxy-2H-cyclopenta[b]furan-4-carboxaldehyde, and the novel cyclopenta(b)furan intermediates of the process.

5 Claims, No Drawings

CERTAIN HEXAHYDRO-2-LOWERALKOXY-5-OXYCYCLOPENTA [b] FURANS CONTAINING AN OLEFINIC SUBSTITUENT IN THE 4-POSITION

This is a division of application Ser. No. 374,850 filed June 9 1973 entitled "Synthesis of Prostaglandins" now abandoned.

SUMMARY OF THE INVENTION

In accordance with this invention, it has been discovered that an oxireno[3,4]cyclopenta[1,2-b]furan of the formula:

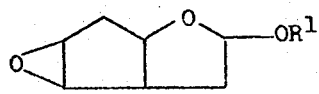   I wherein $R^1$ is lower alkyl;
can be converted to a cyclopenta[b]furan-4-carboxaldehyde of the formula:

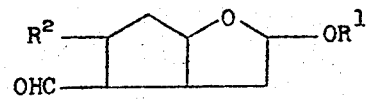   II wherein $R^1$ is as above; and $R_2$ ether hydroxy or hydroxy protected with a hydrolyzable ester or either group;
and that the cyclopenta[b]furan-4-carboxaldehyde of formula II can be expeditiously converted to prostaglandins, particularly prostaglandin $F_{2\alpha}$.

DETAILED DESCRIPTION OF THE INVENTION

As used throughout this application, the term "alkyl" comprehends straight chain and branched chain, saturated aliphatic hydrocarbon groups of 1 to 10 carbon atoms. The preferred alkyl groups are the "lower alkyl" groups, containing 1 to 6 carbon atoms, such as methyl, ethyl, propyl and butyl. In this application, the term "cycloalkyl" comprehends saturated, cyclic, aliphatic hydrocarbon groups of 3 to 7 carbon atoms, such as cyclopropyl, cyclobutyl, cyclopentyl and cyclohexyl. Also in this application, the term "alkenyl" comprehends straight chain and branched chain, aliphatic hydrocarbon groups containing 2 to 10 carbon atoms and one or more carbon to carbon double bonds, such as vinyl, allyl, methallyl, butenyl, hexenyl, heptenyl and octenyl. Further in this application, the term "lower alkoxy" comprehends groups wherein the lower alkyl moiety is as defined above, such as methoxy, ethoxy and butoxy. Still further in this application, the term "aryl" comprehends mononuclear aromatc hydrocarbon groups, such as phenyl and tolyl, which can be unsubstituted or substituted in one or more positions with a lower alkylenedioxy, a halogen, a nitro, a lower alkyl or a lower alkoxy substituent, and polynuclear aryl groups such as naphthyl, anthryl, phenanthryl, and azulyl, which can be unsubstituted or substituted with one or more of the aforementioned groups. The preferred aryl groups are the substituted and unsubstituted mononuclear aryl groups, particularly phenyl. Also herein, the term "lower alkylenedioxy" comprehends alkylenedioxy groups of 1 to 4 carbon atoms, such as methylenedioxy and ethylenedioxy.

As also used throughout this application, the term "hydrolyzable ester or ether group" comprehends any conventional ester or ether, hydroxy protecting group which can be hydrolyzed to yield the hydroxy group. Exemplary ester groups useful for this purpose are those in which the acyl moiety is derived from a lower alkanoic, an aryl lower alkanoic, phosphoric, carbonic or a lower alkane dicarboxylic acid. Among the acids which can be utilized to form such ester groups are the acid anhydrides and the acid halides, preferably chlorides or bromides, with the lower alkanoic acid anhydrides, e.g., acetic anhydride and caproic anhydride, the aryl lower alkanoic acid anhydrides, e.g., benzoic acid anhydride, the lower alkane dicarboxylic acid anhydrides, e.g., succinic anhydride, and the chloroformates, e.g., trichloroethylchloroformate, being preferred. A suitable ether protecting group is, for example, the tetrahydropyranyl ether or 4-methoxy-5,6-dihydro-2-H-pyranyl ether. Others are the arylmethyl ethers, such as benzyl, benzhydryl, or trityl ethers, the α-lower alkoxy-lower alkyl ethers, for example, methoxymethyl, the allylic ethers, and the alkyl silyl ethers, such as trimethyl silyl ether.

As further used throughout this application, in the pictorial representation of the compounds given in this application, a thickened tapered line (▼) indicates a substituent which is in the β-orientation (above the plane of the molecule), a dotted line (——) indicates a substituent which is in the α-orientation (below the plane of the molecule). It is to be understood that the pictorial representations of the compounds given throughout the specification are set forth for convenience and are to be construed as inclusive of other forms, including racemic and optically active forms and are not to be construed as limited to the particular form shown.

As still further used throughout this application, the term "alkali metal" includes lithium, sodium, potassium, rubidium and caesium, unless expressly stated otherwise. Also herein, the term "alkaline earth metal" includes beryllium, magnesium, calcium, strontium and barium, unless expressly stated otherwise. Further herein, the term "dilower alkylamino" comprehends groups wherein the lower alkyl moieties are as defined above.

According to the process of this invention, the oxireno [3,4]cyclopenta[1,2-b]furan of formula I is converted to a prostaglandin via a cyclopenta[b]furan intermediate of formula II.

The cyclopenta[b]furan-4-carboxaldehyde of formula II is obtained by initially reacting the oxireno[3,4-]cyclopenta[1,2-b]furan of formula I with a dialkyl aluminum nitrile to form a 5-hydroxy-4-carbonitrile-cyclopenta[b]furan of the formula:

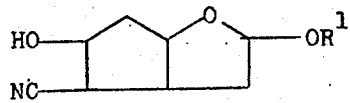   III wherein $R^1$ is as above.

The cyano group in the compound of formula III is then reduced to the corresponding formyl group, after converting, if desired, the 5-hydroxy group to a hydroxy protected with a hydrolyzable ester or ether group, to form the cyclopenta[b]furan-4-carboxaldehyde of formula II.

The cyclopenta[b]furan-4-carboxaldehyde of formula II is also obtained by first reacting the oxireno[3,4]cyclopenta[1,2-b]furan of formula I with an alkali metal salt or alkaline earth metal salt of m- dithiane to form a 4-m-dithian-2-yl-cyclopenta[b]furan-5-ol of the formula:

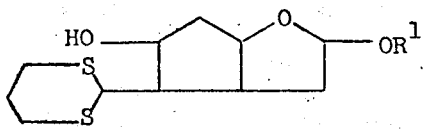

wherein $R^1$ is as above.

The compound of formula IV is then treated with an alkylating agent to alkylate at least one of the sulfur atoms of the 4-dithian-moiety, after converting, if desired, the 5-hydroxy group to a hydroxy protected with a hydrolyzable ester or ether group. The product of the alkylation is then hydrolyzed to produce the cyclopenta[b]furan-4-carboxaldehyde of formula II.

The cyclopenta[b]furan-4-carboxaldehyde of formula II is further obtained by first reacting the oxireno[3,4]cyclopenta[1,2-b]furan of formula I with an acetylide selected from the group consisting of compounds of the formulae:

and

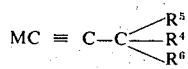

wherein $R^3$ is hydrogen, alkyl, cycloalkyl, alkenyl, phenyl, (lower alkyl)-phenyl or nitrophenyl; $R^4$ and $R^5$ are individually hydrogen or lower alkyl; or $R^4$ and $R^5$ taken together form a cycloalkyl group, $R^6$ is hydroxy or hydroxy protected with a hydrolyzable ester or ether group; and M is an alkali metal or an alkaline earth metal;
to form an acetylenic compound selected from the group consisting of compounds of the formulae:

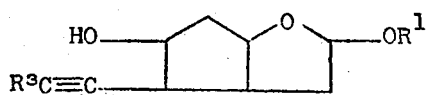

and

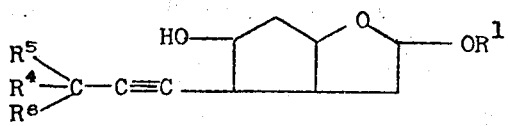

wherein $R^1$, $R^3$, $R^4$, $R^5$ and $R^6$ are as above.

The acetylenic compound of formula VII or VIII is then hydrogenated, after converting, if desired, the 5-hydroxy group to a hydroxy protected with a hydrolyzable ester or ether group, to form an olefinic compound selected from the group consisting of compounds of the formulae:

and

wherein $R^1$, $R^2$, $R^3$, $R^4$, $R^5$ and $R^6$ are as above.

The olefinic compound of formula IX or X is then converted in a conventional manner to the cyclopenta[b]furan-4-carboxaldehyde of formula II by either forming the corresponding 1,2-glycol of the compound of formula IX or X and then cleaving the resulting glycol or by subjecting the olefinic compound of formula IX or X to ozone cleavage.

The oxireno[3,4]cyclopenta[1,2-b]furan of formula I can be converted to a 5-hydroxy-4-carbonitrile-cyclopenta[b]furan of formula III by treatment with a dialkyl aluminum nitrile, preferably a di(lower alkyl) aluminum nitrile, such as diethyl aluminum nitrile or diisobutyl aluminum nitrile. This reaction can be conveniently carried out in a conventional, inert organic solvent. The preferred inert organic solvents for this reaction are the hydrocarbon solvents, such as toluene, and the ether solvents, such as diethyl ether, tetrahydrofuran or dioxane. In this reaction, temperature and pressure are not critical, and the reaction can be suitably carried out at a temperature of 0°C. to reflux and at atmospheric pressure.

The 5-hydroxy group in the compound of formula III can be converted to the corresponding hydroxy group protected with a hydrolyzable ester or ether group in a conventional manner. For example, this conversion can be carried out by treating the 5-hydroxy compound of formula III, in a conventional manner, with dihydropyran in the presence of a catalytic amount of an acid or with a lower alkyl halide in the presence of a base.

The cyano group in the compound of formula III can be reduced, if desired after protecting the 5-hydroxy group, to form the cyclopenta[b]furan-4-carboxaldehyde of formula II by treating the compound of formula III with a reducing agent. The preferred reducing agents are the complex metal hydrides, particularly diisobutyl aluminum hydride. This reaction can be conveniently carried out in a conventional, inert organic solvent, such as a hydrocarbon or an ether solvent, preferably toluene or tetrahydrofuran. In this reaction, temperature and pressure are not critical, and the reaction can be suitably carried out at room temperature and at atmospheric pressure.

The oxireno[3,4]cyclopenta[1,2-b]furan of formula I can be reacted with an alkali metal salt or alkaline earth metal salt of m-dithiane to form the 4-m-dithian-2-yl-cyclopenta[b]furan-5-ol of formula IV in a conventional manner. This reaction is suitably carried out in a conventional, inert organic solvent, such as an ether solvent, preferably diethyl ether, tetrahydrofuran or dioxane. In this reaction, temperature and pressure are not critical, and the reaction can be conveniently carried out at a temperature of from about −30°C. to room temperature and at atmospheric pressure.

The 5-hydroxy group in the compound of formula IV can be converted, if desired, to the corresponding hydroxy protected with a hydrolyzable ester or ether group in a conventional manner, such as set forth above with regard to the 5-hydroxy group in the compound of formula III.

The compound of formula IV can be treated with an alkalating agent to alkylate one of the sulfur atoms of the 4-dithian moiety in a conventional manner. Among the alkylating agents which can be utilized in this reaction are the alkyl halides, such as methyl iodide, and triethyloxonium tetrafluoroborate. In this reaction, temperature and pressure are not critical, and the reaction can be suitably carried out at reflux and atmospheric pressure.

The hydrolysis of the product of the alkylation of the compound of formula IV can be carried out in a conventional manner to produce the cyclopenta[b]furan-4-carboxaldehyde of formula II. For example, the hydrolysis can be suitably carried out in a neutral or slightly acidic medium, such as acetone which contains a trace of water.

The reaction of the oxireno[3,4]cyclopenta[1,2-b]furan of formula I with an acetylide of formula V or VI to form an acetylenic compound of formula VII or VIII can be carried out in a conventional manner in an inert organic solvent. The preferred solvents in this reaction are the ethers, such as tetrahydrofuran, diethyl ether, or dioxane. In this reaction, temperature and pressure are not critical and the reaction can be suitably carried out at reflux temperature and atmospheric pressure.

The 5-hydroxy group in the acetylenic compounds of formulae VII and VIII can be converted, if desired, to the corresponding hydroxy protected with a hydrolyzable ester or ether group in a conventional manner, such as set forth above with respect to the 5-hydroxy group in the compound of formula III.

The acetylenic compound of formula VII or VIII can be hydrogenated in a conventional manner to form the olefinic compound of formula IX or X. This hydrogenation is preferably carried out in accordance with the procedure described in U.S. Pat. No. 2,681,938.

The olefinic compound of formula IX or X can be converted to the cyclopenta[b]furan-4-carboxaldehyde of formula II in a conventional manner by either forming the corresponding 1,2-glycol and then cleaving the glycol or by subjecting the olefinic compound of formula IX or X to ozone cleavage. The preferred method for converting the olefinic compound of formula IX or X to the cyclopenta[b]furan-4-carboxaldehyde is by ozone cleavage. The ozone cleavage of the olefinic compound of formula IX or X can be carried out in a conventional manner in an inert organic solvent. The preferred inert organic solvents are the aliphatic hydrocarbons, such as petroleum ether; ethyl acetate; the chlorinated hydrocarbons, such as methylene chloride, and the lower alkanols, such as methanol. This reaction can be suitably carried out by blowing ozone through the mixture of olefinic compound of formula IX or X and the inert organic solvent at low temperature, preferably at −70°C. Reductive working-up of the resulting ozonide in a conventional manner, such as by hydrogenating the ozonide in ethyl acetate in the presence of palladium on calcium carbonate, can be conveniently utilized to form the desired cyclopenta[b]furan-4-carboxaldehyde of formula II.

Prostaglandins are obtained by first reacting the cyclopenta[b]furan-4-carboxaldehyde of formula II with a phosphonate of the formula:

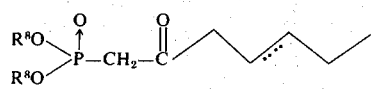   XI wherein $R^8$ is lower alkyl or aryl; and the dotted bond can be optionally hydrogenated;
or with a phosphonane of the formula:

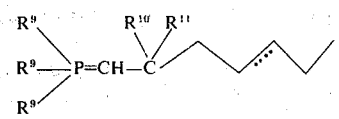   XII wherein $R^9$ is aryl or diloweralkylamino; $R^{10}$ individually hydroxy; $R^{11}$ is individually hydrogen; or $R^{10}$ and $R^{11}$ taken together are oxo; and the dotted bond can be optionally hydrogenated;
to yield a compound of the formula:

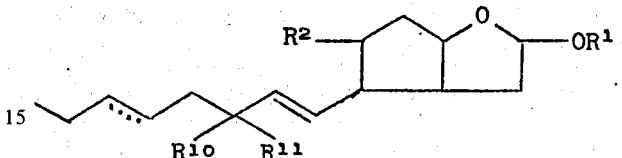   XIII wherein $R^1$, $R^2$, $R^{10}$, $R^{11}$ and the dotted bond are as above.

The reaction of the cyclopenta[b]furan-4-carboxaldehyde of formula II with the phosphonate of formula XI can be carried out utilizing conventional Horner-reaction conditions. Preferably, this reaction is carried out in the presence of a base, preferably in the presence of a inert organic solvent. In this reaction, any conventional base and inert organic solvent can be utilized. The preferred bases are, however, the alkali metal hydrides, such as sodium hydride, preferably dissolved in a solvent such as benzene, toluene, dimethylformamide, tetrahydrofuran, dioxane or 1,2-dimethoxyethane, and the alkali metal alcoholates, such as sodium methylate, dissolved in an alcohol, such as methanol. Although temperature and pressure are not critical, this reaction is preferably effected between about −20°C. and the boiling temperature of the solvent, especially between about 0°C. and room temperature (22°C.), and at atmospheric pressure.

The reaction of the cyclopenta[b]furan-4-carboxaldehyde with the phosphorane of formula XII can be carried out utilizing conventional Wittig-reaction conditions. Preferably, this reaction is carried out in the presence of catalytic amounts of an organic acid. In this reaction, any conventional organic acid such as the lower alkanoic acids and benzoic acid can be utilized. Generally, this reaction is carried out in an inert organic solvent such as benzene, toluene, dimethylformamide, 1,2-dimethoxyethane or dioxane. Although temperature and pressure are not critical in this reaction, temperatures between about room temperature (22°C.) and the boiling point of the solvent and atmospheric pressure are preferred.

If desired, the compound of formula XIII in which $R^{10}$ and $R^{11}$, taken together, are oxo can be reduced with a complex metal hydride to give a compound of formula XIII in which $R^{10}$ is hydroxy and $R^{11}$ is hydrogen. This reduction can be carried out in a conventional manner. Preferably, the reduction is carried out by treating the compound of formula XIII with zinc borohydride or a complex borane, or, when $R^2$ is other than hydrogen, with $NaBH_4$ in methanol.

The compound of formula XIII wherein $R^{10}$ is hydroxy and the dotted bond is hydrogenated can be converted in a conventional manner to Prostaglandin $F_{2\alpha}$. In accordance with the procedure of Corey et al., Tetrahedron Letters 311–313 (1970), the 4-(3-hydroxy-1-octenyl) compound of formula XIII can be converted to Prostaglandin $F_{2\alpha}$, utilizing the Wittig reagent derived from 5-triphenylphosphoniopentanoic acid.

The acid hydrolysis of the acetylenic compound of formula VIII, wherein $R_6$ is hydroxy or hydroxy protected with a hydrolyzable ester or ether group and one of $R_4$ and $R_5$ is a pentyl group, can be carried out in a conventional manner. Preferably, the acetylenic compound is reacted with a dilute mineral acid, such as hydrochloric acid, in the presence of acetonitrile. By this procedure, the corresponding lactol of the compound of formula VIII is formed, and the ester or ether, hydroxy-protecting group ($R_6$) is removed.

The process of this application offers a new, economic access to the pharmacologically interesting prostaglandin class of compounds. The compounds of formulae II, III, IV, VII, VIII, IX, X and XIII are therefore of value as intermediates for the manufacture of prostaglandins.

The compounds of formulae II, III, IV, VII, VIII, IX, X and XIII can be present as optically and geometrically different isomers. Preferred among such compounds are those having a stereoconfiguration of the formula:

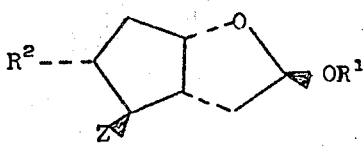   XV wherein Z is the 4-formyl group given in formula II or one of the 4-side-chains given in formulae III, IV, VII, VIII, IX, X or XIII; and $R^1$ and $R^2$ are as above.
The compounds of formula XV can be obtained by utilizing, as the starting material, an oxireno[3,4-]cyclopenta[1,2-b]furan having a stereo-configuration of the formula:

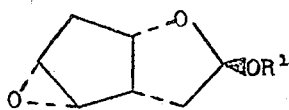   I-A wherein $R^1$ is as above.

Generally, the oxireno[3,4]cyclopenta[b]furan starting materials of formula I can be obtained by etherifying a compound of the formula:

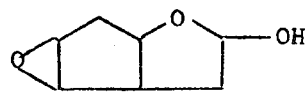   XVI in a conventional manner. Preferably, the etherification is carried out by reacting the compound of formula XVI with a lower alkanol in the presence of an acid catalyst. Any conventional acid catalyst can be utilized in carrying out this reaction. Among the preferred acid catalysts are acidic cation exchange resins, such as a polystyrene sulfonic acid resin; inorganic acids such as sulfuric acid; Lewis acids, such as boron trifluoride, aluminum trichloride, etc.; and organic acids, such as p-toluenesulfonic acid. Generally the lower alkanol can serve as the solvent medium. In carrying out this reaction, temperatures of from −40° to 10°C. are utilized. The preferred catalyst for use in this reaction is boron trifluoride.

The compounds of formula I-A and the optically active antipodes thereof, which are the preferred starting materials, can be obtained in accordance with the procedure described in U.S. Pat. Application Ser. No. 331,931, filed Feb. 12, 1973, of Chadha, Partridge and Uskokovic, entitled "Asymmetric Synthesis of Optically Active Prostaglandins" and now abandoned.

An optically active compound of formula I-A can also be obtained by first resolving a lactone of the formula:

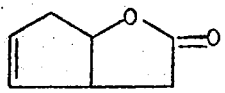   XVII to separate the antipode of desired optical activity, then epoxidizing the antipode, reducing the 2-keto group on the antipode to a 2-hydroxy group, and then etherifying the 2-hydroxy group. In this procedure, the resolution, epoxidation, reduction, and etherification steps can be carried out in a conventional manner to maintain the optical activity of the antipodes. However, the preferred resolving agent is optically active α-phenethylamine.

The optically active starting materials of formula I can be utilized in accordance with the process of his application to yield optically active prostaglandins. The optically active starting materials of formula I-A are particularly valuable for making optically active Prostaglandin $F_{2\alpha}$. The optically active stereoconfiguration of the antipodes of formula I is carried through the entire reaction sequence. Therefore, the process of this application affords an expedient procedure for producing a prostaglandin in either of its optically active forms, depending on the optical activity of the starting material of formula I.

The examples which follow further illustrate this invention. (2aα,5aα,5bα)-hexahydro-4α-methoxy-1aαH-oxireno[3,4]cyclopenta[1,2-b]-furan is (1aR,-2aS,4R,5,5aS,5bS)-hexahydro-4-methoxy-2H-oxireno[3,4]-cyclopenta[1,2-b]furan. Alox is aluminum oxide; Alox (Act I) is aluminum oxide, activity I.

EXAMPLE 1

To 1.56 g of (2aα,5aα,5bα)-hexahydro-4α-methoxy-1a H-oxireno[3,4]-cyclopenta[1,2-b]furan, dissolved in 20 ml of toluene, is added dropwise, within 10 minutes under an argon atmosphere and with stirring at 0°C., 16.7 ml of a 1.8 molar solution of diethyl aluminum cyanide in toluene and the mixture is stirred at 0°C. for a further 45 minutes. To the almost colorless mixture is added dropwise a mixture of 20 ml of methanol and 0.5 ml of water, and the resulting gel is stirred at room temperature (22°C.) for 20 minutes, filtered through Celite diatomaceous earth, which is covered with anhydrous sodium sulphate, and rinsed with methanol. The clear filtrate is evaporated under a water-jet vacuum to give a colorless oil, which soon crystallizes. Recrystallization from methylene chloride/hexane yields 1.0g of pure (3aα,6aα)-hexahydro-4β-hydroxy-2α-methoxy-2H-cyclopenta[b]furan-5α-carbonitrile; melting point 138°–139°C.

By concentration of the mother liquors, there crystallizes a mixture of 4α- and 5α-nitriles and finally almost pure (3aα,6aα)-hexahydro-5β-hydroxy-2α-methoxy-2H-cyclopenta[b]furan-4α-carbonitrile, which is obtained in analytically pure form by recrystallization from diethyl ether/heptane; melting point 74°–75°C.

EXAMPLE 2

2.4 g of m-dithiane is dissolved in 20 ml of anhydrous tetrahydrofuran and treated under an argon atmosphere at −30°C. with 9 ml of a 2-molar solution of methyl lithium in diethyl ether. There is added dropwise thereto at −30°C. a solution of 1.50 g of (2aα,-5aα,5bα)-hexahydro-4α-methoxy-1aαH-oxireno[3,4-]cyclopenta[1,2-b]furan in 10 ml of tetrahydrofuran. The mixture is stirred for 1 hour at −30°C. and then for a further 21 hours at room temperature (22°C.). The mixture is poured on to ice-water, extracted with ethyl acetate and washed with aqueous sodium chloride solution until neutral. After drying the solution over sodium sulphate and removing the solvent on a rotary evaporator, there is obtained 4.4 g of an orange-colored, partially crystalline mass, from which the major portion of the excess dithiane is sublimated off at 80°–90°C. under a high vacuum.

The residue (3.7 g) is chromatographed on a column of neutral Alox I. A total of 2.335 g (84.6%) of the two isomers 4α-m-dithian-2-yl-(3aα,6aα)-hexahydro-2α-methoxy-2H-cyclopenta[b]furan-5β-ol and 5α-m-dithian-2-yl-(3aα,6aα)-hexahydro-2α-methoxy-2H-cyclopenta[b]furan-4β-ol is eluted with diethyl ether, 1.2 g of the 4β-alcohol crystallizing from the first two ether fractions. Recrystallization from methylene chloride/diethyl ether/heptane gives colorless crystals of the 4β-alcohol; melting point 121°–122°C.

From the later chromatogram fractions, after repeated layer chromatography, the colorless, isomeric 5β-alcohol is isolated as an oil which crystallizes; melting point 74°–75°C.

EXAMPLE 3

Under an argon atmosphere and with stirring at 0°–5°C., 10 ml of a 2-M solution of methyl lithium in diethyl ether is added to 1.92 g of 1-heptyne in 10 ml of tetrahydrofuran. The mixture is subsequently allowed to warm to room temperature (22°C.), and a solution of 1.56 g of (2aα,5aα,5bα)-hexahydro-4α-methoxy-1aαH-oxireno[3,4]cyclopenta[1,2-b]furan in 10 ml of tetrahydrofuran is added dropwise. The light-yellow, clear solution is maintained at reflux for 66 hours. Thereafter, it is poured on to ice, taken up in ethyl acetate, washed with aqueous sodium chloride solution until neutral, and dried over sodium sulphate, and the solvent is removed. The orange-colored residue (2.6 g) is filtered through Alox (Act I, 60 g). After elution with benzene/diethyl ether (2:1 parts by volume) and then with diethyl ether alone, a total of 1930 mg (76.6%) of a 1:1 mixture (parts by wt.) of 4α-(1-heptynyl)-(3aα,-6aα)-hexahydro-2α-methoxy-2H-cyclopenta[b]furan-5β-ol and 5α(1-heptynyl)-(3aα,6aα)-hexahydro-2α-methoxy-2H-cyclopenta[b]furan-4β-ol is obtained as a colorless oil. Separation is achieved by means of column chromatography with diisopropylether as the eluant.

The polar zone in the thin-layer chromatogram is 4α-(1-heptynyl)-(3aα,6aα)-hexahydro-2α-methoxy-2H-cyclopenta [b]furan-5β-ol.

EXAMPLE 4

915 mg of (3aα,6aα)-hexahydro-5β-hydroxy-2α-methoxy-2H-cyclopenta[b]furan-4α-carbonitrile, dissolved in 10 ml of absolute tetrahydrofuran, is mixed at room temperature (22°C.) with 10.5 mmol of a solution of diisobutyl aluminum hydride in toluene, and the resulting clear solution is stirred for 48 hours under argon. At 0°C., 5 ml of methanol and 1 ml of water are added dropwise, and the mixture is stirred for 0.5 hour. Ethyl acetate is then added, the mixture is dried over sodium sulphate, and the solvent is removed. There is obtained 865 mg of (3aα,6aα)-hexahydro-5β-hydroxy-2α-methoxy-2H-cyclopenta[b]furan-4α-carboxaldehyde as a yellowish oil.

EXAMPLE 5

553 mg of 4α-m-dithian-2-yl-(3aα,6aα)-hexahydro-2α-methoxy-2H-cyclopenta[b]furan-5β-ol, dissolved in 5 ml of acetone, is maintained at reflux in the presence of 0.5 ml of water, 5 ml of methyl iodide and 0.5 g of soda for 5 hours, after which time no more starting marterial is detected. The mixture is taken up in diethyl ether, washed with water, and dried, and the solvent is removed. 270 mg of (3aα,6aα)-hexahydro-5β-hydroxy-2α-methoxy-2H-cyclopenta[b]furan-4α-carboxaldehyde is obtained.

EXAMPLE 6

504 mg of 4α-(1-heptynyl)-(3aα,6aα)-hexahydro-2α-methoxy-2H-cyclopenta[b]furan-5β-ol is dissolved in 15 ml of methylene chloride and hydrogenated in the presence of 250 mg of Lindlar catalyst (described in U.S. Pat. No. 2,681,938) and 20 mg of triethylamine. After 2 hours and the uptake of 1 equivalent of hydrogen, the catalyst is filtered off under a vacuum, and the methylene chloride solution is washed with water and dried. Removal of the solvent gives 500 mg of 4α-(1-cis-heptenyl)-(3aα,6aα)-hexahydro-2α-methoxy-2H-cyclopenta[b]furan-5β-ol as a colorless oil.

EXAMPLE 7

508 mg of 4α-(1-cis-heptenyl)-(3aα,6aα)-hexahydro-2α-methoxy-2H-cyclopenta[b]furan-5β-ol, dissolved in 10 ml of ethyl acetate, is ozonized at −70°C. After 0.5 hour, nitrogen is blown through the mixture in place of ozone, the mixture is warmed to −40°C., and 372 mg of trimethylphosphite is added. After warming up, the solvent is removed at 0°C., and the mixture is taken up in methylene chloride and filtered through 5 g of Alox I. The solvent and resulting caproaldehyde are removed under a high vacuum. There is obtained 345 mg of (3aα,6aα)-hexahydro-5β-hydroxy-2α-methoxy-2H-cyclopenta[b]furan-4α-carboxaldehyde as a colorless oil.

EXAMPLE 8

310 mg of a 55% suspension of sodium hydride in oil is washed twice with dry pentane and then suspended in 30 ml of dry monoglyme (ethyleneglycol-dimethylether). With stirring 1.7 g of dimethyl-2-oxoheptylphosphonate in 10 ml of monoglyme is added dropwise to form a white precipitate. To this 1.15 g of (3aα)-hexahydro-5β-hydroxy-2α-methoxy-2H-cyclopenta[b]furan-4α-carboxaldehyd in 10 ml monoglyme is added over a period of 10 minutes after which time the reaction mixture is stirred for 1½ hours. Adjustment of the pH to 6–7 by the addition of ice-cold 0.1 N hydrochloric acid and extraction with ethylacetate gives 1.95 g of a yellowish oil which upon chromatography on Silica gel furnishes 975 mg of 1-[(3aα,6aα)-hexahydro-5β-hydroxy-2α-methoxy-2H-cyclopenta[b]-furan-4α-yl]-1-octen-3-one.

EXAMPLE 9

564 mg of 1-[(3aα,6aα)-hexahydro-5β-hydroxy-2α-methoxy-2H-cyclopenta[b]furan-4α-yl]-1-octen-3-one is dissolved in 7 ml of methylene chloride, 1 ml of pyridine and 0.5 ml of acetic anhydride and stirred for 6 hours at 50°C. Then, the solvent and the excess reagent are removed under a vacuum, and the residue is dissolved in benzene, dried again under a vacuum, and finally dried under a high vacuum. The contents of the flask are dissolved in 5 ml of 1,2-dimethoxyethane and stirred with 1.3 equivalents of a freshly prepared solution of zinc borohydride in diethyl ether, for 2 hours at room temperature (22°C.). The mixture is cooled to 0°C., 2 ml of methanol and 0.5 ml of aqueous potassium carbonate solution is added, and the resulting mixture is stirred for 20 minutes at room temperature (22°C.), then taken up in ethyl acetate, and washed with aqueous sodium chloride solution. After drying and removal of the solvent, there is obtained 518 mg of (3aα,6aα)-hexahydro-4α-(3-hydroxy-1-octenyl)-2α-methoxy-2H-cyclopenta[b]-furan-5β-ol.

EXAMPLE 10

980 mg of (3aα,6aα)-hexahydro-2α-methoxy-4α-[3-(hydroxy)-1-octenyl]-2H-cyclopenta[b]furan-5β-ol is dissolved in 5 ml of acetonitrile and 2 ml of 0.03-N aqueous hydrochloric acid and is stirred for 2 hours at room temperature (22°C.). The mixture is taken up in ethyl acetate, washed with water, and dried, and the solvent is removed. The residue is dissolved in 3 ml of absolute dimethyl sulphoxide and added to a solution of sodium 5-triphenylphosphonium valerate in dimethyl sulphoxide. The mixture is stirred for 4 hours at room temperature, poured on to ice-water, and extracted several times with pentane. The pentane solution is dried over sodium sulphate, the pentane is removed, and the residue is purified on Alox I. There is obtained 950 mg of cis-7-[3α,5α-dihydroxy-2β-(3-hydroxy-1-octenyl)-1α-cyclopentyl]-5-heptenoic acid, i.e., a mixture of C₁₅-epimers of racemic Prostaglandin F₂ α in the form of a colorless oil.

EXAMPLE 11

3.0 g of cis-3,3a,6,6a-tetrahydro-2H-cyclopenta(b)furan-2-one and 5.0 g of (−)-(S)-α-phenylethylamine is maintained for 18 hours under argon at 80°C. The yellowish oil is taken up in ethyl acetate and is separated from the excess amine by washing with 0.5 N hydrochloric acid. The solution is then washed with saturated, aqueous sodium chloride, dried over sodium sulphate and compressed with a rotary evaporator. From a mixture of dichloromethane, diethyl ether and hexane, the desired, left-rotatory diastereomer (A) is crystallized; melting point 99°–100°C.

A recrystallization from the same solvent mixture yields optically pure (−)-5R-hydroxy-N-(α-S-methybenzyl)-2-cyclopenten-1S-acetamide, (A); melting point 101°–102°C.;[α]$_D^{20}$ −120.5° (c=1,CHCl₃).

The mother liquor is chromatographed on a 50-fold quantity of Kieselgel, and the other diastereomer is eluted from the Kieselgel with diethyl ether/methylene-chloride (3:1 parts by volume). Recrystallization with ethyl acetate/hexane yields wad-like, clear crystals of (−)-5S-hydroxy-N-(α-S-methylbenzyl)-2-cyclopenten-1R-acetamide (B); melting point 72°–73°C.; [α]$_D^{20}$−75.2° (c=1,CHCl₃).

1.0 g of the amide (A) in 10 ml of 20 percent by weight, aqueous caustic soda and 2 ml of methanol is heated for 2½ hours in a 100°C. heated oil bath, thereby causing the starting material to competely disappear. The cooled solution is poured into ice-cold 2 normal hydrochloric acid and extracted twice with ethyl acetate. The organic phase is washed with aqueous sodium chloride, dried over sodium sulphate and the solvent removed. The remaining, colorless oil is crystallized from diethyl ether/hexane to yield (−)-5R-hydroxy-2-cyclopenten-1S-acetic acid lactone; melting point 47.5°–48.5°C.; [α] $_D^{20}$ −90.0° (c=1,CHCl₃).

Utilizing the foregoing procedure, the diastereomer (B) yields(+)-5S-hydroxy-2-cyclopenten-1R-acetic acid lactone; melting point 47°–48°C.; [α] $_D^{20}$ +92.6° (C=1,CHCl₃).

We claim:
1. A compound of the formula:

wherein R¹ is lower alkyl; R² is selected from the group consisting of hydroxy, tetrahydropyranyloxy, 4-methoxy-5,6-dihydro-2-H-pyranyloxy, benzyloxy, trityloxy, benzhydryloxy, alphaloweralkoxyloweralkoxy, trimethylsilyloxy, and hydroxy-protected as its ester, said ester being hydrolyzable and derived from phosphoric acid, lower alkanoic acid, aryl lower alkanoic acid, carbonic acid, and lower alkane dicarboxylic acid;

R³ is hydrogen, an alkyl group of from 1–10 carbon atoms, a cycloalkyl group of 3–7 carbon atoms, an alkenyl group of from 2–10 carbon atoms, phenyl, (lower alkyl)-phenyl or nitrophenyl.

2. The compound of claim 1 having a stereoconfiguration of the formula:

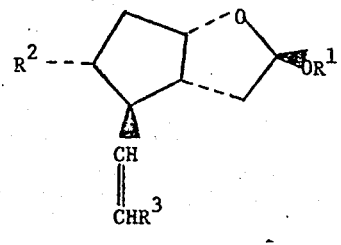

wherein R¹, R² and R³ are as above;
its optically active antipode or a racemate thereof.

3. The compound of claim 2 wherein said compound is 4α-(1-cis-heptenyl)-(3aα,6aα)-hexahydro-2α-methoxy-2H-cyclopenta[b]furan-5β-ol.

4. A compound of the formula:

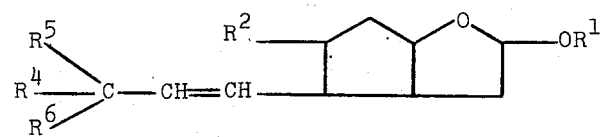

wherein R¹ is lower alkyl; R² and R⁶ are selected from the group consisting of hydroxy, tetrahydropyranyloxy, 4-methoxy-5,6-dihydro-2-H- pyranyloxy, benzyloxy, trityloxy, benzhydryloxy, alphaloweralkoxyloweralkoxy, trimethylsilyloxy, and hydroxy-protected as its ester, said ester being hydrolyzable and derived from phosphoric acid,
lower alkanoic acid,
aryl lower alkanoic acid,
carbonic acid,
and lower alkane dicarboxylic acid;
$R^4$ and $R^5$ may be taken together to form a cycloalkyl group having from 3–7 carbon atoms.

5. The compound of claim 4 having a stereoconfiguration of the formula:

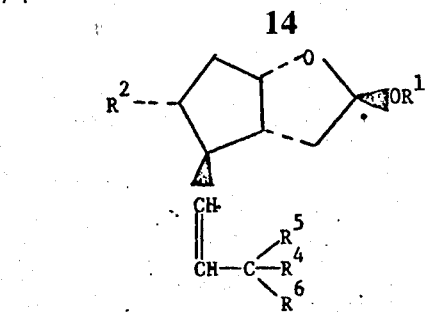

wherein $R^1$, $R^2$, $R^4$, $R^5$ and $R^6$ are as above; its optically active antipode or a racemate thereof.

* * * * *

UNITED STATES PATENT AND TRADEMARK OFFICE
CERTIFICATE OF CORRECTION

PATENT NO. : 3,970,674
DATED : July 20, 1976
INVENTOR(S) : HANS JOHANN MAYER, ALBERT EDUARD FISCHLI AND
MICHAEL JOSEF KLAUS It is certified that error appears in the above-identified patent and that said Letters Patent are hereby corrected as shown below:

Cover Sheet -

Related U.S. Application Data

(62) June 9, 1973   should be    June 29, 1973

Column 1, line 7, "June 9, 1973"

should be

June 29, 1973.

Signed and Sealed this

Thirty-first Day of May 197

[SEAL]

Attest:

RUTH C. MASON
Attesting Officer

C. MARSHALL DANN
Commissioner of Patents and Trademarks